US008052987B2

(12) United States Patent
Horowitz et al.

(10) Patent No.: US 8,052,987 B2
(45) Date of Patent: Nov. 8, 2011

(54) METHOD OF ADMINISTERING BISPHOSPHONATES

(75) Inventors: Zebulun D. Horowitz, Basking Ridge, NJ (US); Peter C. Richardson, Far Hills, NJ (US); Ulrich Trechsel, Luzein (CH)

(73) Assignee: Novartis Pharmaceuticals Corporation, East Hanover, NJ (US)

( * ) Notice: Subject to any disclaimer, the term of this patent is extended or adjusted under 35 U.S.C. 154(b) by 861 days.

(21) Appl. No.: 10/311,942

(22) PCT Filed: Jun. 18, 2001

(86) PCT No.: PCT/EP01/06850
§ 371 (c)(1),
(2), (4) Date: Mar. 25, 2003

(87) PCT Pub. No.: WO01/97788
PCT Pub. Date: Dec. 27, 2001

(65) Prior Publication Data
US 2003/0181421 A1 Sep. 25, 2003

Related U.S. Application Data

(60) Provisional application No. 60/267,689, filed on Feb. 9, 2001, provisional application No. 60/367,354, filed on Jun. 20, 2000.

(51) Int. Cl.
*A61F 2/02* (2006.01)
(52) U.S. Cl. ...................................... 424/423
(58) Field of Classification Search .................. 424/426, 424/423, 434, 449, 451, 464; 523/113, 114, 523/116
See application file for complete search history.

(56) References Cited

U.S. PATENT DOCUMENTS

| | | | |
|---|---|---|---|
| 4,761,406 A | 8/1988 | Flora et al. | |
| 4,812,304 A | 3/1989 | Anderson et al. | |
| 4,812,311 A | 3/1989 | Uchtman | 424/112 |
| 4,822,609 A | 4/1989 | Flora | 424/112 |
| 4,939,130 A | 7/1990 | Jaeggi et al. | |
| 5,366,965 A | 11/1994 | Strein | 514/102 |
| 5,616,560 A | 4/1997 | Geddes et al. | 514/12 |
| 5,730,715 A | 3/1998 | Sage, Jr. et al. | |
| 5,965,547 A | 10/1999 | Goodship et al. | |
| 5,994,329 A | 11/1999 | Daifotis et al. | 514/108 |
| 6,015,801 A * | 1/2000 | Daifotis et al. | 514/108 |
| 6,225,294 B1 | 5/2001 | Daifotis et al. | 514/108 |
| 6,255,288 B1 | 7/2001 | Goodship et al. | |
| 2001/0001306 A1 | 5/2001 | Daifotis et al. | 514/108 |
| 2001/0002395 A1 | 5/2001 | Daifotis et al. | 514/108 |
| 2001/0018431 A1 | 8/2001 | Daifotis et al. | 514/102 |
| 2001/0044427 A1 | 11/2001 | Mazel et al. | 514/102 |

FOREIGN PATENT DOCUMENTS

| | | |
|---|---|---|
| DE | 198 53 483 | 5/1999 |
| EP | 0 105 196 A2 | 4/1984 |
| EP | 0 162 510 B1 | 11/1985 |
| EP | 0 210 728 | 6/1986 |
| EP | 0 210 728 B1 | 2/1987 |
| EP | 0 381 296 B1 | 8/1990 |
| EP | 0600834 | 6/1994 |
| EP | 0 648 120 | 4/1995 |
| EP | 1 051 976 | 11/2000 |
| EP | 1 175 904 A2 | 1/2002 |
| GB | 2 177 001 | 6/1986 |
| GB | 2 177 001 | 10/1987 |
| GB | 2 336 311 | 10/1999 |
| JP | A-62-048627 | 6/1986 |
| WO | WO 93/11786 | 6/1993 |
| WO | WO 96/07417 | 3/1996 |
| WO | WO 96/07418 | 3/1996 |
| WO | WO9712619 | 4/1997 |
| WO | WO 97/47356 | 12/1997 |
| WO | WO 98/57656 | 12/1998 |
| WO | WO 99/04773 | 2/1999 |
| WO | WO 99/15155 | 4/1999 |
| WO | WO 99/18972 | 4/1999 |
| WO | WO 00/71104 | 11/2000 |
| WO | WO 01/15703 | 3/2001 |
| WO | WO 01/45636 | 6/2001 |
| WO | WO0189494 | 11/2001 |
| WO | WO0197788 | 12/2001 |

OTHER PUBLICATIONS www.fda.gov/medwatch/safety/2008/Jun__PI/Reclast__PI.pdf.*
J.J. Body, M.D., Ph.D., Cancer, vol. 80, Issue S8, pp. 1699-1701.*
Hacking et al. "Disodium Pamidronate (AREDIA), Single Infusion Monotherapy (90 mg) Compared to Repeated Cycles of 30 mg for Symptomatic Treatment of Breast Cancer bone Metastases" Eur. J. Cancer, 27, Suppl. 2, S570, 1991.
Ryan et al, "Intravenous 3 Aminohydroxypropylidene 1.1 Biphosphonate (APD) in the Treatment of Pagets Disease", Br. J. Rheumatol. (29, Abstr. Suppl. 2, 139, 1990).
Bombassei et al. "Effects of Intravenous Pamidronate Therapy on Paget's Disease of Bone", The American Journal of American Sciences, vol. 308, No. 4, pp. 226-233, (1994).
H. Fleisch, "The Bisphosphonate Ibandronate, Given Daily as Well as Discontinuously, Decreases Bone Resorption and Increases Calcium Retention as Assessed by $^{45}Ca$ Kinetics in the Intact Rat", Osteoporosis Int., vol. 6, pp. 166-170, (1996).
Roldan et al, "Clinical Application of Bisphosphonate's Pharmacokinetic Principles" Medicina, 57 Suppl 1 pp. 76-82, 1997 (English Translation of Aplicacion Clinica de los Principios Farmacocineticos de los Bisfosfonatos).

(Continued)

Primary Examiner — Carlos Azpuru
(74) Attorney, Agent, or Firm — McCarter & English, LLP

(57) ABSTRACT

The invention relates to bisphosphonates, in particular more potent N-bisphosphonates such as zoledronic acid and derivatives, and to methods of treatment using bisphosphonates. These bisphosphonates are used with satisfactory results for prolonged inhibition of bone resorption in conditions of abnormally increased bone turnover, e.g. osteoporosis, by intermittent administration, the periods between bisphosphonate administrations are longer than was previously considered appropriate, e.g. a dosing interval of at least about 6 months or less frequently.

9 Claims, No Drawings

OTHER PUBLICATIONS

Filipponi et al., "Intermittent Versus Continuous Clodronate Administration in Postmenopausal Women with Low Bone Mass", Bone, vol. 26, No. 3, pp. 269-274, (2000).

Boutsen et al, "Primary Prevention of Glucocorticoid-induced Osteoporosis with Intravenous Pamidronate and Calcium: a Prospective Controlled One-Year study Comparing a Single Infusion, a 3-Monthly Therapy and Calcium Alone", Arthritis Rheum, vol. 43, No. 9, Suppl., S383 (2000).

Boutsen et al, "Primary Prevention of Glucocorticoid-Induced Osteoporosis with Intravenous Pamidronate and Calcium: A Prospective Controlled 1-Year Study Comparing a Single Infusion, an Infusion Given Once Every 3 Months, and Calcium Alone", Journal of Bone and Mineral Research, vol. 16, No. 1, pp. 1-13 (2001).

Glorieux et al, "Cyclic Administration of Pamidronate in Children with Severe Osteogenesis Inperfecta", The New England Journal of Medicine, vol. 339, No. 14, pp. 947-952, (2004).

Khan et al, "Comparison of Three Intravenous Regimens of Clodronate in Paget Disease of Bone", Journal of Bone and Mineral Research, vol. 11, No. 2, pp. 178-182, (1996).

Pepersack et al, "Paget's Disease of Bone: Five Regimens of Pamidronate Treatment", Clinical Rheumatology, vol. 13, No. 1, pp. 39-44, (1994).

Peretz et al, "Cyclical Pamidtronate Infusions in Postmenopausal Osteoporosis", Maturitas: Journal of the Climacteric & PostMenopause, vol. 25, pp. 69-75, (1996).

Pfeilschifter et al., "Effect of Pamidronate on Clinical Symptoms and Bone Metabolisn in Fibrous Dysplasia and McCune-Albright-Syndrom", Medizinische Klinik vol. 93, No. 6, pp. 352-359, (1998) (English translation of Wirkung von Pamidronat auf Beschwerdebild and Knochenstoffwechsel bei Bibroser Dysplasie McCune-Albright Symdrom).

Theibaud et al, "A Single Infusion of the Bisphosphonate AHPrBP (APD) as Treatment of Pagent's Disease of Bone", The American Journal of Medicine, vol. 85, pp. 207-212 (1988).

Giannini et al., "Effects of One-Year Cyclical Treatment with Clodronate on Postmenopausal Bone Loss", Bone, vol. 14, pp. 137-141 (1993).

Giannini et al., "Continuous and Cyclical Clodronate Therapies and Bone Density in Postmenopausal Bone Loss", Obstet. Gynecol., vol. 88, No. 3, pp. 431-436 (1996).

Heikkinen et al., "Short-Term Intravenous Bisphosphonates in Prevention of Postmenopausal Bone Loss", J. Bone Miner. Res., vol. 12, No. 1, pp. 103-110 (1997).

Lee et al., "Cyclic Pamidronate Infusion Improves Bone Mineralisation and Reduces Fracture Incidence in Osteogenesis Imperfecta", Eur. J. Pediatr., vol. 160, No. 11, pp. 641-644 (2001).

Sorbera et al., "Zoledronate Disodium", Drugs Fut., vol. 25, No. 3, pp. 259-268 (2000).

"Zoledronic Acid", Adis R&D Insight (2000—abstract).

"Drug Updates", R&D Focus (2000—abstract).

Storm et al., "Effect of Intermittent Cyclical Etidronate Therapy on Bone Mass and Fracture Rate in Women with Postmenopausal Osteoporosis", NEJM, vol. 322, No. 18, pp. 1265-1271 (1990).

Watts et al., "Intermittent Cyclical Etidronate Treatment of Postmenopausal Osteoporosis", NEJM, vol. 323, No. 2, pp. 73-79 (1990).

Lunar News Apr. 1997, p. 1-42.

M. Passeri (1991) "Intermittent treatment with intravenous 4-amino-1-hydroxyutylidene-1,1-bisphosphonate (AHBuBP) in the therapy of postmenopausal osteoporosis" Bone and Mineral, 15: 237-248.

S.D. Vasikaran et al. (1995) "Sustained Response to Intravenous Alendronate in Postmenopausal Osteoporosis" Bone 17:6 517-520.

The Merck Manual, 1999, Chapter 59, Nonarticular Rheumatism, pp. 474-482.

Need, Allan G., et al. "Vitamin D Status: Effects on Parathyroid Hormone and 1,25-Dihydroxyvitamin D in Postmenopausal Women"; The American Journal of Clinical Nutrition, vol. 71, No. 6, Jun. 6, 2000; pp. 1577-1581.

Binkley, Neil, et al. "Zoledronate Prevents the Development of Absolute Osteopenia Following Ovariectomy in Adult Rhesus Monkeys", Journal of Bone and Mineral Research, vol. 13, No. 11, 1998, pp. 1775-1782.

Body, J.J., et al. A Dose-Finding Study of Zoledronate in Hypercalcemic Cancer Patients, Journal of Bone and Mineral Research, vol. 14, No. 9, 1999, pp. 1557-1561.

Buckler, H., et al. "Single Infusion of Zoledronate in Paget's Disease of Bone: A Placebo-Controlled, Dose-Ranging Study", Bone, vol. 24, No. 5, Supplement, May 1999, pp. 81S-85S.

"Use of Bisphosphonates in Metabolic Bone Diseases", National Institute of Health Osteoporosis and Related Bone Diseases—National Resource Center, Bethesda, Maryland, 7 Pages.

Clark, NW, et al. "Disodium Pamidronate Identifies Differential Osteoclastic Bone Resorption in Metastatic Prostate Cancer"; British Journal of Urology (1992), 69, pp. 64-70.

Osteogenesis Imperfecta (OI)—Internet website—www.childrensorthopaedics.com/osteogenesis_imperfecta.html; 1 Page.

Hill, P.A., et al. "Bone Remodelling"; British Journal of Orthodontics, vol. 25, May 1998, pp. 101-107.

Roodman, G. David, et al. "Mechanisms of Abnormal Bone Turnover in Paget's Disease"; internet website, www.sciencedirect.com; Apr. 22, 1999, pp. 1-4.

Reid, Ian R., et al., "Intravenous Zoledronic Acid in Postmenopausal Women with Low Bone Mineral Density"; The New England Journal of Medicine, vol. 346, No. 9, Feb. 28, 2002, pp. 653-661.

Black, Dennis M., et al., "Once-Yearly Zoledronic Acid for Treatment of Postmenopausal Osteoporosis", The New England Journal of Medicine, vol. 356, No. 18, May 3, 2007, pp. 1809-1822.

Seeman, E., et al., "Non-Compliance: The Achilles' Heel of Antifracture Efficacy", Osteoporos Int. (2007) 18: pp. 711-719.

Recker, Robert R., et al., "Effect of Dosing Frequency on Bisphosphonate Medication Adherence in a Large Longitudinal Cohort of Women", Mayo Clinic Proc. Jul. 2005, 80 (7): pp. 856-861.

Cramer, Joyce A., et al., "The Effect of Dosing Frequency on Compliance and Persistence with Bisphosphonate Therapy in Postmenopausal Women: A Comparison of Studies in the United States, the United Kingdom, and France", Clinical Therapeutics, vol. 28, No. 10, (2006), pp. 1686-1694.

Cramer, J.A., et al., "A Systematic Review of Persistence and Compliance with Bisphosphonates for Osteoporosis", Osteoporos Int. (2007) 18: pp. 1023-1031.

Briesacher, Becky A., et al., "Consequences of Poor Compliance with Bisphosphonates", Bone, 41 (2007) pp. 882-887.

Reid, David M., et al. "Zoledronic Acid and Risedronate in the Prevention and Treatment of Glucocorticoid-Induced Osteoporosis (HORIZON): A Multicentre, Double-Blind, Double-Dummy, randomised Controlled Trial", Lancet, vol. 373, Apr. 11, 2009, pp. 1253-1263.

Thiebaud, D., et al., "Three Monthly Intravenous Injections of Ibandronate in the Treatment of Postmenopausal Osteoporosis", The American Journal of Medicine, vol. 103, Oct. 1997, pp. 298-307.

Christiansen, C., et al., "Dose Dependent Effects on Bone Resorption and Formation of Intermittently Administered Intravenous Ibandronate", Osteoporosis International, vol. 14, (2003), pp. 609-613.

Lyles, Kenneth W., et al., "Zoledronic Acid and Clinical Fractures and Mortality After Hip Fracture", The New England Journal of Medicine, Nov. 1, 2007, vol. 357, No. 18, pp. 1799-1809.

Claxton, Ami J., et al., "A Systematic Review of the Association Between Dose Regimens and Medication Compliance", Clinical Therapeutics, vol. 23, No. 8, (2001), pp. 1296-1310.

Gatti et al., "New Bisphosphonates in the Treatment of Bone Diseases", Drugs & Aging, vol. 15, No. 4. 285-296, (1999).

Khan et al, "Elimination and Biochemical Responses to Intravenous Alendronate in Postmenopausal Osteoporosis", Journal of Bone and Mineral Research, vol. 12, No. 10 (1997).

J. H. Lin "Bisphosphonates: A Review of Their Pharmacokinetic Properties", Bone, vol. 18, No. 2, pp. 75-85, (1996).

Green et al., "Preclinical Pharmacology of CGP 42 ' 446, a New, Potent Heterocyclic Bisphosphonate Compound", Journal of Bone and Mineral Research, vol. 9, No. 5, (1994).

Woitge, Henning W., et al., "Short- and Long Term Effects of Ibandronate Treatment on Bone Turnover in Paget Disease of Bone", Clinical Chemistry, May 2000, vol. 46, No. 5, pp. 684-690.

Brinkley, Neil, et al., "Zoledronate Prevents the Development of Absolute Osteopenia Following Ovariectomy in Adult Rhesus Monkeys", Journal of Bone and Mineral Research, vol. 13, No. 11, 1998, pp. 1775-1782.

Body, J.J., M.D., Ph.D., "Clinical Research Update—Zoledronate", Skeletal Complications of Malignancy, Cancer Supplement, Oct. 15, 1997, vol. 80, No. 8, pp. 1699-1701.

Administrative Decision (2008) Gao Xing Zhong Zi No. 378 issued by Beijing Superior People's Court of the Peoples Republic of China, pp. 1-10.

"Treatment of Tumor-Induced Hypercalcemia Angiogenesis Inhibitor", Drugs of the Future, 2000, Prous Science, 25 (3), pp. 259-268.

Muller, Klaus, et al., "Effects of the Bisphosphonate Zoledronate on Bone Loss in the Ovariectomized and in the Adjuvant Arthritic Rat", Arzneim-Forsch/Drug Res. vol. 48 (I), No. 1 (1998), pp. 81-86.

Chakravarty, Kuntal, et al., "A Single Infusion of Bisphosphonate AHPrBP in the Treatment of Paget's Disease of Bone", The Journal of Rheumatology, Nov. 1994, vol. 21, No. 11, pp. 2118-2121.

Watts, R.A. et al., "Treatment of Paget's Disease of Bone with Single Dose Intravenous Pamidronate", Annals of the Rheumatic Diseases, 1993, 52, pp. 616-618.

Grauer, Andreas, et al., "Long-Term Efficacy of Intravenous Pamidronate in Paget's Disease of Bone", Seminars in Arthritis and Rheumatism, Feb. 1994, vol. 23, No. 4, pp. 283-284.

Broggini, M., et al., "Short Courses of Intravenous Clodronate in the Treatment of Paget's Disease of Bone: A Long-Term Follow-Up Trial", International Journal of Clinical Pharm. Res. vol. 13, No. 6, (1993), pp. 301-304.

Clohisy, Denis R., et al., "Localized, Tumor-Associated Osteolysis Involves the Recruitment and Activation of Osteoclasts", Journal of Orthopaedic Research, vol. 14, No. 1, (1996), pp. 2-6.

Guise, Theresa A., M.D., "Molecular Mechanisms of Osteolytic Bone Metastases", Skeletal Complications of Malignancy, Cancer Supplement, Jun. 15, 2000, vol. 88, No. 12, pp. 2892-2898.

Riggs, B., Lawrence, "The Mechanisms of Estrogen Regulation of Bone Resorption" The Journal of Clinical Investigation, Nov. 2000, vol. 106, No. 10, pp. 1203-1204.

Eastell, Richard, et al., "Bone Formation Rate in Older Normal Women: Concurrent Assessment with Bone Histomorphometry, Calcium Kinetics, and Biochemical Markers", Journal of Clinical Endocrinology and Metabolism, 1988, vol. 67, No. 4, pp. 741-748.

Delmas, Pierre D., et al., "Urinary Excretion of Pyridinoline Crosslinks Correlates with Bone Turnover Measured on Iliac Crest Biopsy in Patients with Vertebral Osteoporosis" Journal of Bone and Mineral Research, vol. 6, No. 6, 1991, pp. 639-644.

Garnero, Patrick, et al., "Increased Bone Turnover in Late Postmenopausal Women Is a Major Determinant of Osteoporosis", Journal of Bone and Mineral Research, vol. 11, No. 3, 1996, pp. 337-349.

Stepan, J.J., et al., "Bone Loss and Biochemical Indices of Bone Remodeling in Surgically Induced Postmenopausal Women", Bone, vol. 8, (1987), pp. 279-284.

Heaney, Robert P., et al., "Menopausal Changes in Bone Remodeling", Journal Lab. Clin. Med., Dec. 1978, vol. 92, No. 6, pp. 964-970.

Liu, Zhong-hou, et al., "Treatment and Prevention of Osteoporosis", Osteoporosis, Jan. 1998, pp. 226 and 227.

"Osteoporosis and its Pharmacological Treatment", Textbook Series for 21st Century: Special Clinical Pharmacy, Beijing Medical University Press, 1st Edition, Sep. 1999, pp. 248-256.

* cited by examiner

METHOD OF ADMINISTERING BISPHOSPHONATES

This application is a 371 of International Application No. PCT/EP01/06850, which claims benefit of U.S. Prov. Application 60/267,689, filed Feb. 9, 2001 and U.S. Provisional Application 60/367,354, filed on Jun. 20, 2000.

This invention relates to bisphosphonates, in particular to the pharmaceutical use of bisphosphonates in the treatment of conditions of abnormally increased bone turnover, such as osteoporosis.

Bisphosphonates are widely used to inhibit osteoclast activity in a variety of both benign and malignant diseases in which bone resorption is increased. Thus bisphosphonates have recently become available for long-term treatment of patients with Multiple Myeloma (MM). These pyrophosphate analogs not only reduce the occurrence of skeletal related events but they also provide patients with clinical benefit and improve survival. Bisphosphonates are able to prevent bone resorption in vivo; the therapeutic efficacy of bisphosphonates has been demonstrated in the treatment of Paget's disease of bone, tumour-induced hypercalcemia and, more recently, bone metastasis and multiple myeloma (MM) (for review see Fleisch H 1997 Bisphosphonates clinical. In Bisphosphonates in Bone Disease. From the Laboratory to the Patient. Eds: The Parthenon Publishing Group, New York/London pp 68-163). The mechanisms by which bisphosphonates inhibit bone resorption are still poorly understood and seem to vary according to the bisphosphonates studied. Bisphosphonates have been shown to bind strongly to the hydroxyapatite crystals of bone, to reduce bone turn-over and resorption, to decrease the levels of hydroxyproline or alkaline phosphatase in the blood, and in addition to inhibit both the activation and the activity of osteoclasts.

In addition bisphosphonates have been proposed for use in the treatment of osteoporosis. Thus for instance, as described in U.S. Pat. No. 4,812,304 (Procter & Gamble) a method has been proposed for treating or preventing osteoporosis in humans comprising administering to a subject afflicted with or at risk to osteoporosis a bone cell activating compound and a bone resorption inhibiting polyphosphonate according to a regime consisting of one or more cycles, whereby each cycle consists of: (a) a bone activating period of from about 1 day to about 5 days during which a bone cell activating amount of a bone cell activating compound is administered to said subject; followed by (b) a bone resorption inhibition period of from about 10 days to about 20 days during which ethane-1-hydroxy-1,1-diphosphonic acid, or a pharmaceutically acceptable salt or ester thereof, is administered daily to said subject in an amount from about 0.25 mgP/kg/day to about 3.3 mgP/kg/day; followed by (c) a rest period of from about 70 days to about 180 days during which the subject receives neither a bone cell activating compound nor a bone resorption inhibiting polyphophonate.

Also, for example, U.S. Pat. No. 4,761,406 (Procter & Gamble) proposes a method for treating osteoporosis, in humans or lower animals afflicted with or at risk of osteoporosis, comprising administering to said human or lower animal an effective amount of a bone resorption inhibiting polyphosphonate according to the following schedule: (a) a period of from about 1 day to about 90 days during which said bone resorption inhibiting polyphosphonate is administered daily in a limited amount, followed by (b) a rest period of from about 50 days to about 120 days, and (c) repeating (a) and (b) two or more times where a net increase in bone mass of said human or animal results.

Surprisingly we have now found that bisphosphonates, in particular more potent nitrogen-containing bisphosphonates, can be used for prolonged inhibition of bone resorption in conditions of abnormally increased bone turnover by intermittent administration, wherein the periods between bisphosphonate administrations are longer than was previously considered appropriate to achieve satisfactory treatment. In particular and contrary to expectation we have found that satisfactory treatment results can be obtained even when the dosing intervals greatly exceed the natural bone remodelling cycle.

Accordingly the present invention provides a method for the treatment of conditions of abnormally increased bone turnover in a patient in need of such treatment which comprises intermittently administering an effective amount of a bisphosphonate to the patient, wherein the period between administrations of bisphosphonate is at least about 6 months or at least about once a year.

The invention further provides use of a bisphosphonate in the preparation of a medicament for the treatment of conditions of abnormally increased bone turnover in which the bisphosphonate is administered intermittently and in which the period between administrations of bisphosphonate is at least about 6 months or at least about once a year.

Conditions of abnormally increased bone turnover which may be treated in accordance with the present invention include: treatment of postmenopausal osteoporosis, e.g. to reduce the risk of osteoporotic fractures; prevention of postmenopausal osteoporosis, e.g. prevention of postmenopausal bone loss; treatment or prevention of male osteoporosis; treatment or prevention of corticosteroid-induced osteoporosis and other forms of bone loss secondary to or due to medication, e.g. diphenylhydantoin, thyroid hormone replacement therapy; treatment or prevention of bone loss associated with immobilisation and space flight; treatment or prevention of bone loss associated with rheumatoid arthritis, osteogenesis imperfecta, hyperthyroidism, anorexia nervosa, organ transplantation, joint prosthesis loosening, and other medical conditions. For example, such other medical conditions may include treatment or prevention of periarticular bone erosions in rheumatoid arthritis; treatment of osteoarthritis, e.g. prevention/treatment of subchondral osteosclerosis, subchondral bone cysts, osteophyte formation, and of osteoarthritic pain, e.g. by reduction in intra-osseous pressure; treatment or prevention of hypercalcemia resulting from excessive bone resorption secondary to hyperparathyroidism, thyrotoxicosis, sarcoidosis or hypervitaminosis D.

Thus in the present description the terms "treatment" or "treat" refer to both prophylactic or preventative treatment as well as curative or disease modifying treatment, including treatment of patients at risk of contracting the disease or suspected to have contracted the disease as well as patients who are ill or have been diagnosed as suffering from a disease or medical condition. In particularly preferred embodiments the invention may be used for the prophylactic treatment of osteoporosis and similar diseases. Thus for example, bisphosphonate may be administered to individuals at risk of developing osteoporosis on a regular basis at dosing intervals of at least about 6 months, e.g. bisphosphnates may be administered routinely to postmenopausal women at dosing intervals of once every 6 months or less frequently, e.g. annually.

In accordance with the present invention the bisphosphonate dosing interval is at least about 6 months, e.g. once every 180 days, or less frequently, conveniently once a year, or at any interval in between, e.g. once every 7, 8, 9, 10, or 11 months. Dosing intervals of greater than once per year may be used, e.g. about once every 18 months or about once every 2 years, or even less frequently, e.g. a frequency of up to about once every 3 years or less often.

The bisphosphonates used in the present invention are typically those which inhibit bone resorption. Such compounds characteristically contain two phosphonate groups attached to a single carbon atom, forming a "P—C—P" structure, e.g. in a compound of formula I

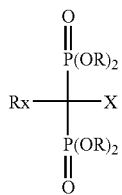

wherein
X is hydrogen, hydroxyl, amino, alkanoyl, or an amino group mono- or disubstituted by $C_1$-$C_4$ alkyl;
R is hydrogen or $C_1$-$C_4$ alkyl and
Rx is an optionally substituted hydrocarbyl group,
and pharmaceutically acceptable salts thereof or any hydrate thereof.

Thus, for example, suitable bisphosphonates for use in the invention may include the following compounds or a pharmaceutically acceptable salt thereof, or any hydrate thereof: 3-amino-1-hydroxypropane-1,1-diphosphonic acid (pamidronic acid), e.g. pamidronate (APD); 3-(N,N-dimethylamino)-1-hydroxypropane-1,1-diphosphonic acid, e.g. dimethyl-APD; 4-amino-1-bydroxybutane-1,1-diphosphonic acid (alendronic acid), e.g. alendronate; 1-hydroxy-ethidene-bisphosphonic acid, e.g. etidronate; 1-hydroxy-3-(methylpentylamino)-propylidene-bisphosphonic acid, (ibandronic acid), e.g. ibandronate; 6-amino-1-hydroxyhexane-1,1-diphosphonic acid, e.g. amino-hexyl-BP; 3-(N-methyl-N-n-pentylamino)-1-hydroxypropane-1,1-diphosphonic acid, e.g. methyl-pentyl-APD (=BM 21.0955); 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate, including N-methyl pyridinium salts thereof, for example N-methyl pyridinium iodides such as NE-10244 or NE-10446; 1-(4-chlorophenylthio)methane-1,1-diphosphonic acid (tiludronic acid), e.g. tiludronate; 3-[N-(2-phenylthioethyl)-N-methylamino]-1-hydroxypropane-1,1-diphosphonic acid; 1-hydroxy-3-(pyrrolidin-1-yl)propane-1,1-diphosphonic acid, e.g. EB 1053 (Leo); 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U-81581 (Upjohn); 1-hydroxy-2-(imidazo[1,2-a]pyridin-3-yl)ethane-1,1-diphosphonic acid, e.g. YM 529; and 1,1-dichloromethane-1,1-diphosphonic acid (clodronic acid), e.g. clodronate; YM175.

Preferred bisphosphonates for use in the present invention are N-bisphosphonates, i.e. compounds which in addition to the characteristic geminal bisphosphonates moiety (e.g. "P—C—P") comprise a nitrogen-containing side chain, e.g. a compound of formula I'

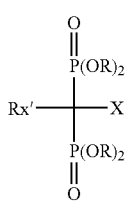

wherein
X is hydrogen, hydroxyl, amino, alkanoyl, or an amino group mono- or disubstituted by $C_1$-$C_4$ alkyl;
R is hydrogen or $C_1$-$C_4$ alkyl and
Rx' is a side chain which contains an optionally substituted amino group, or a nitrogen containing heterocycle (including aromatic nitrogen-containing heterocycles),
and pharmaceutically acceptable salts thereof or any hydrate thereof.

Thus, for example, suitable N-bisphosphonates for use in the invention may include the following compounds or a pharmaceutically acceptable salt thereof, or any hydrate thereof: 3-amino-1-hydroxypropane-1,1-diphosphonic acid (pamidronic acid), e.g. pamidronate (APD); 3-(N,N-dimethylamino)-1-hydroxypropane-1,1-diphosphonic acid, e.g. dimethyl-APD; 4-amino-1-hydroxybutane-1,1-diphosphonic acid (alendronic acid), e.g. alendronate; 1-hydroxy-3-(methylpentylamino)-propylidene-bisphosphonic acid, ibandronic acid, e.g. ibandronate; 6-amino-1-hydroxyhexane-1,1-diphosphonic acid, e.g. amino-hexyl-BP; 3-(N-methyl-N-n-pentylamino)-1-hydroxypropane-1,1-diphosphonic acid, e.g. methyl-pentyl-APD (=BM 21.0955); 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate, including N-methyl pyridinium salts thereof, for example N-methyl pyridinium iodides such as NE-10244 or NE-10446; 3-[N-(2-phenylthioethyl)-N-methylamino]-1-hydroxypropane-1,1-diphosphonic acid; 1-hydroxy-3-(pyrrolidin-1-yl)propane-1,1-diphosphonic acid, e.g. EB 1053 (Leo); 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U-81581 (Upjohn); and 1-hydroxy-2-(imidazo[1,2-a]pyridin-3-yl)ethane-1,1-diphosphonic acid, e.g. YM 529.

In one embodiment a particularly preferred N-bisphosphonate for use in the invention comprises a compound of Formula II

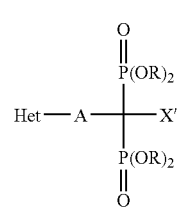

wherein
Het is an imidazole, oxazole, isoxazole, oxadiazole, thiazole, thiadiazole, pyridine, 1,2,3-triazole, 1,2,4-triazole or benzimidazole radical, which is optionally substituted by alkyl, alkoxy, halogen, hydroxyl, carboxyl, an amino group optionally substituted by alkyl or alkanoyl radicals or a benzyl radical optionally substituted by alkyl, nitro, amino or aminoalkyl;
A is a straight-chained or branched, saturated or unsaturated hydrocarbon moiety containing from 1 to 8 carbon atoms;
X' is a hydrogen atom, optionally substituted by alkanoyl, or an amino group optionally substituted by alkyl or alkanoyl radicals, and
R is a hydrogen atom or an alkyl radical,
and the pharmacologically acceptable salts thereof.

In a further embodiment a particularly preferred bisphosphonate for use in the invention comprises a compound of Formula III

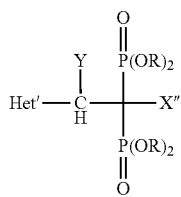

wherein
Het' is a substituted or unsubstituted heteroaromatic five-membered ring selected from the group consisting of imidazolyl, imidazolinyl, isoxazolyl, oxazolyl, oxazolinyl, thiazolyl, thiazolinyl, triazolyl, oxadiazolyl and thiadiazolyl wherein said ring can be partly hydrogenated and wherein said substituents are selected from at least one of the group consisting of $C_1$-$C_4$ alkyl, $C_1$-$C_4$ alkoxy, phenyl, cyclohexyl, cyclohexylmethyl, halogen and amino and wherein two adjacent alkyl substituents of Het can together form a second ring;
Y is hydrogen or $C_1$-$C_4$ alkyl;
X" is hydrogen, hydroxyl, amino, or an amino group substituted by $C_1$-$C_4$ alkyl, and
R is hydrogen or $C_1$-$C_4$ alkyl;
as well as the pharmacologically acceptable salts and isomers thereof.

In a yet further embodiment a particularly preferred bisphosphonate for use in the invention comprises a compound of Formula IV

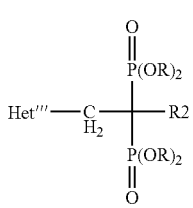

wherein
Het''' is an imidazolyl, 2H-1,2,3-, 1H-1,2,4- or 4H-1,2,4-triazolyl, tetrazolyl, oxazolyl, isoxazolyl, oxadiazolyl, thiazolyl or thiadiazolyl radical which is unsubstituted or C-mono- or di-substituted by lower alkyl, by lower alkoxy, by phenyl which may in turn be mnon- or di-substituted by lower alkyl, lower alkoxy and/or halogen, by hydroxy, by di-lower alkylamino, by lower alkylthio and/or by halogen and is N-substituted at a substitutable N-atom by lower alkyl or by phenyl-lower alkyl which may in turn be mono- or di-substituted in the phenyl moiety by lower alkyl, lower alkoxy and/or halogen, and
R2 is hydrogen, hydroxy, amino, lower alkylthio or halogen, lower radicals having up to and including 7 C-atoms,
or a pharmacologically acceptable salt thereof.

Examples of particularly preferred N-bisphophonates for use in the invention are:
2-(1-Methylimidazol-2-yl)-1-hydroxyethane-1,1-diphosphonic acid;
2-(1-Benzylimidazol-2-yl)-1-hydroxyethane-1,1-diphosphonic acid;
2-(1-Methylimidazol-4-yl)-1-hydroxyethane-1,1-diphosphonic acid;
1-Amino-2-(1-methylimidazol-4-yl)ethane-1,1-diphosphonic acid;
1-Amino-2-(1-benzylimidazol-4-yl)ethane-1,1-diphosphonic acid;
2-(1-Methylimidazol-2-yl)ethane-1,1-diphosphonic acid;
2-(1-Benzylimidazol-2-yl)ethane-1,1-diphosphonic acid;
2-(Imidazol-1-yl)-1-hydroxyethane-1,1-diphosphonic acid;
2-(Imidazol-1-yl)ethane-1,1-diphosphonic acid;
2-(4H-1,2,4-triazol-4-yl)-1-hydroxyethane-1,1-diphosphonic acid;
2-(Thiazol-2-yl)ethane-1,1-diphosphonic acid;
2-(Imidazol-2-yl)ethane-1,1-diphosphonic acid;
2-(2-Methylimidazol-4(5)-yl)ethane-1,1-diphosphonic acid;
2-(2-Phenylimidazol-4(5)-yl)ethane-1,1-diphosphonic acid;
2-(4,5-Dimethylimidazol-1-yl)-1-hydroxyethane-1,1-diphosphonic acid, and
2-(2-Methylimidazol-4(5)-yl)-1-hydroxyethane-1,1-diphosphonic acid,
and pharmacologically acceptable salts thereof.

The most preferred N-bisphosphonate for use in the invention is 2-(imidazol-1yl)-1-hydroxyethane-1,1-diphosphonic acid (zoledronic acid) or a pharmacologically acceptable salt thereof.

Pharmacologically acceptable salts are preferably salts with bases, conveniently metal salts derived from groups Ia, Ib, IIa and IIb of the Periodic Table of the Elements, including alkali metal salts, e.g. potassium and especially sodium salts, or alkaline earth metal salts, preferably calcium or magnesium salts, and also ammonium salts with ammonia or organic amines.

Especially preferred pharmaceutically acceptable salts are those where one, two, three or four, in particular one or two, of the acidic hydrogens of the bisphosphonic acid are replaced by a pharmaceutically acceptable cation, in particular sodium, potassium or ammonium, in first instance sodium.

A very preferred group of pharmaceutically acceptable salts is characterized by having one acidic hydrogen and one pharmaceutically acceptable cation, especially sodium, in each of the phosphonic acid groups.

The bisphosphonic acid derivatives specifically mentioned above are well known from the literature. This includes their manufacture (see e.g. EP-A-513760, pp. 13-48). For example, 3-amino-1-hydroxypropane-1,1-diphosphonic acid is prepared as described e.g. in U.S. Pat. No. 3,962,432 as well as the disodium salt as in U.S. Pat. Nos. 4,639,338 and 4,711,880, and 1-hydroxy-2-(imidazol-1-yl)-ethane-1,1-diphosphonic acid is prepared as described e.g. in U.S. Pat. No. 4,939,130.

The bisphosphonates (hereinafter referred to as the Agents of the Invention) may be used in the form of an isomer or of a mixture of isomers where appropriate, typically as optical isomers such as enantiomers or diastereoisomers or geometric isomers, typically cis-trans isomers. The optical isomers are obtained in the form of the pure antipodes and/or as racemates.

The Agents of the Invention can also be used in the form of their hydrates or include other solvents used for their crystallisation.

The Agents of the Invention are preferably used in the form of pharmaceutical compositions that contain a therapeutically effective amount of active ingredient optionally together with or in admixture with inorganic or organic, solid or liquid, pharmaceutically acceptable carriers which are suitable for administration.

The Agents of the Invention may be administered alone or in combination with other bone active drugs, either in fixed combinations or separately both physically and in time, including hormones, such as a steroid hormone, e.g. an estrogen; a partial estrogen agonist, or estrogen-gestagen combination, a calcitonin or an analogue or derivative thereof, e.g. salmon, eel or human calcitonin parathyroid hormone or analogues thereof, e.g. e.g. PTH (1-84), PTH (1-34), PTH (1-36), PTH (1-38), PTH (1-31)$NH_2$ or PTS 893; a SERM (Selective Estrogen Receptor Modulator) e.g. raloxifene, lasofoxifene, TSE424, FC1271, Tibolone (Livial®); vitamin D or an analog. Such additional bone active drugs may be administered more frequently than the bisphosphonate.

The pharmaceutical compositions may be, for example, compositions for enteral, such as oral, rectal, aerosol inhalation or nasal administration, compositions for parenteral, such as intravenous or subcutaneous administration, or compositions for transdermal administration (e.g. passive or iontophoretic).

Preferably, the pharmaceutical compositions are adapted to oral or parenteral (especially intravenous, subcutaneous, intramuscular, or transdermal) administration. Intravenous and oral, first and foremost intravenous administration is considered to be of particular importance. Preferably the bisphosphonate active ingredient is in the form of a parenteral, most preferably an intravenous form.

The particular mode of administration and the dosage may be selected by the attending physician taking into account the particulars of the patient, especially age, weight, life style, activity level, hormonal status (e.g. post-menopausal) and bone mineral density as appropriate.

The dosage of the Agents of the Invention may depend on various factors, such as effectiveness and duration of action of the active ingredient, e.g. including the relative potency of the bisphosphonate used, mode of administration, warm-blooded species, and/or sex, age, weight and individual condition of the warm-blooded animal.

Normally the dosage is such that a single dose of the bisphosphonate active ingredient from 0.005-20 mg/kg, especially 0.01-10 mg/kg, is administered to a warm-blooded animal weighing approximately 75 kg.

"mg/kg" means mg drug per kg body weight of the mammal—including man—to be treated.

The dose mentioned above is typically administered intermittently with a period of at least 6 months between doses. The period between bisphosphonate administrations may be longer, e.g. conveniently once per year, once per 18 months or once every 2 years, or even longer, or any period in between.

Formulations in single dose unit form contain preferably from about 1% to about 90%, and formulations not in single dose unit form contain preferably from about 0.1% to about 20%, of the active ingredient. Single dose unit forms such as ampoules of infusion solution or solid for preparation of infusion solution doses, capsules, tablets or dragées contain e.g. from about 0.5 mg to about 500 mg of the active ingredient. It will be appreciated that the actual unit dose used will depend upon the potency of the bisphosphonates, the dosing interval and route of administration amongst other things. Thus the size of the unit dose is typically lower for more potent bisphosphonates and greater the longer the dosing interval. For example, for more potent, N-bisphosphonates such as zoledronic acid a unit dose of from about 1 up to about 10 mg may be used for parenteral, e.g. intravenous, administration. For example, also for more potent N-bisphosphonates a unit dose of from about 1 to about 5 mg may be used parenterally for dosing once every 6 months; whereas a dose of from about 2 up to about 10 mg may be used for once a year parenteral dosing.

Unit doses may be administered as a single or divided dose, i.e. a dose in which the unit dose is divided into two or more equal or unequal parts and in which the parts are administered to the patient at the same time, during overlapping time periods or at separate time points. When the unit dose is administered as a divided dose at separate time points, the interval between the separate administrations of the divided dose may be from hours, e.g. 1 hour, up to about 1 month (approximately 30 days). In accordance with the invention, the time interval between administration of the last part of the divided dose and administration of the first part of the next, following divided dose is at least 6 months or longer, e.g. about 1 year.

Thus, for example, a 10 mg unit dose may be administered as two equal 5 mg parts at an interval of about 1 week to about 1 month, e.g. about 2 weeks, between administration of the parts. Alternatively, for example, a 5 mg unit dose may be administered as two unequal parts of 4 mg and 1 mg (or 3 mg and 2 mg) at an interval of from 1 to 3 days to 1 to 3 weeks, e.g. about 1 week, between administration of the parts.

Pharmaceutical preparations for enteral and parenteral administration are, for example, those in dosage unit forms, such as dragées, tablets or capsules and also ampoules. They are prepared in a manner known per se, for example by means of conventional mixing, granulating, confectioning, dissolving or lyophilising processes. For example, pharmaceutical preparations for oral administration can be obtained by combining the active ingredient with solid carriers, where appropriate granulating a resulting mixture, and processing the mixture or granulate, if desired or necessary after the addition of suitable adjuncts, into tablets or dragée cores.

Suitable carriers are especially fillers, such as sugars, for example lactose, saccharose, mannitol or sorbitol, cellulose preparations, and also binders, such as starch pastes, using, for example, corn, wheat, rice or potato starch, gelatin, tragacanth, methylcellulose and/or polyvinylpyrrolidone and, if desired, disintegrators, such as the above-mentioned starches, also carboxymethyl starch, crosslinked polyvinylpyrrolidone, agar or alginic acid or a salt thereof, such as sodium alginate. Adjuncts are especially flow-regulating agents and lubricants, for example silicic acid, talc, stearic acid or salts thereof, such as magnesium or calcium stearate, and/or polyethylene glycol. Dragee cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Colouring substances or pigments may be added to the tablets or dragee coatings, for example for the purpose of identification or to indicate different doses of active ingredient.

Other orally administrable pharmaceutical preparations are dry-filled capsules made of gelatin, and also soft, sealed capsules made of gelatin and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and, where appropriate, stabilisers. In soft capsules the active ingredient is preferably dissolved or suspended in suitable liquids, such as fatty oils, paraffin oil or liquid polyethylene glycols, it being possible also for stabilisers to be added.

Parenteral formulations are especially injectable fluids that are effective in various manners, such as, intramuscularly, intraperitoneally, intranasally, intradermally, subcutaneously or preferably intravenously. Such fluids are preferably isotonic aqueous solutions or suspensions which can be prepared before use, for example from lyophilised preparations which contain the active ingredient alone or together with a pharmaceutically acceptable carrier, or from solution concentrates. The pharmaceutical preparations may be sterilised and/or contain adjuncts, for example preservatives, stabilisers, wetting agents and/or emulsifiers, solubilisers, salts for regulating the osmotic pressure and/or buffers.

Suitable formulations for transdermal application include an effective amount of the active ingredient with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the active ingredient to the skin of the host at a controlled and predetermined rate over a prolonged period of time, and means to secure the device to the skin.

The following Examples illustrate the invention described hereinbefore.

In the following Examples the term "active ingredient" is to be understood as being any one of the bisphosphonic acid derivatives mentioned above as being useful according to the present invention.

EXAMPLES

Example 1

Capsules containing coated pellets of active ingredient, for example, disodium pamidronate pentahydrate, as active ingredient:

| Core pellet: | |
|---|---|
| active ingredient (ground) | 197.3 mg |
| Microcrystalline cellulose (Avicel ® PH 105) | 52.7 mg |
| | 250.0 mg |
| + Inner coating: | |
| Cellulose HP-M 603 | 10.0 mg |
| Polyethylene glycol | 2.0 mg |
| Talc | 8.0 mg |
| | 270.0 mg |
| + Gastric juice-resistant outer coating: | |
| Eudragit ® L 30 D (solid) | 90.0 mg |
| Triethyl citrate | 21.0 mg |
| Antifoam ® AF | 2.0 mg |
| Water | |
| Talc | 7.0 mg |
| | 390.0 mg |

A mixture of disodium pamidronate with Avicel® PH 105 is moistened with water and kneaded, extruded and formed into spheres. The dried pellets are then successively coated in the fluidized bed with an inner coating, consisting of cellulose HP-M 603, polyethylene glycol (PEG) 8000 and talc, and the aqueous gastric juice-resistant coat, consisting of Eudragit® L 30 D, triethyl citrate and Antifoam® AF. The coated pellets are powdered with talc and filled into capsules (capsule size 0) by means of a commercial capsule filling machine, for example Höfliger and Karg.

Example 2

Monolith adhesive transdermal system, containing as active ingredient, for example, 1-hydroxy-2-(imidazol-1-yl)-ethane-1,1-diphosphonic acid:

| Composition: | |
|---|---|
| polyisobutylene (PIB) 300 (Oppanol B1, BASF) | 5.0 g |
| PIB 35000 (Oppanol B10, BASF) | 3.0 g |
| PIB 1200000 (Oppanol B100, BASF) | 9.0 g |
| hydrogenated hydrocarbon resin (Escorez 5320, Exxon) | 43.0 g |
| 1-dodecylazacycloheptan-2-one (Azone, Nelson Res., Irvine/CA) | 20.0 g |
| active ingredient | 20.0 g |
| Total | 100.0 g |

Preparation:

The above components are together dissolved in 150 g of special boiling point petroleum fraction 100-125 by rolling on a roller gear bed. The solution is applied to a polyester film (Hostaphan, Kalle) by means of a spreading device using a 300 mm doctor blade, giving a coating of about 75 g/m$^2$. After drying (15 minutes at 60° C.), a silicone-treated polyester film (thickness 75 mm, Laufenberg) is applied as the peel-off film. The finished systems are punched out in sizes in the wanted form of from 5 to 30 cm$^2$ using a punching tool. The complete systems are sealed individually in sachets of aluminised paper.

Example 3

Vial containing 1.0 mg dry, lyophilized 1-hydroxy-2-(imidazol-1-yl)ethane-1,1-diphosphonic acid (mixed sodium salts thereof). After dilution with 1 ml of water, a solution (concentration 1 mg/ml) for i.v. infusion is obtained.

| Composition: | |
|---|---|
| active ingredient (free diphosphonic acid) | 1.0 mg |
| mannitol | 46.0 mg |
| Trisodium citrate × 2 H$_2$O | ca. 3.0 mg |
| water | 1 ml |
| water for injection | 1 ml. |

In 1 ml of water, the active ingredient is titrated with trisodium citrate×2 H$_2$O to pH 6.0. Then, the mannitol is added and the solution is lyophilized and the lyophilisate filled into a vial.

Example 4

Ampoule containing active ingredient, for instance disodium pamidronate pentahydrate dissolved in water. The solution (concentration 3 mg/ml) is for i.v. infusion after dilution.

| Composition: | |
|---|---|
| active ingredient | 19.73 mg |
| (≙ 5.0 mg of anhydrous active ingredient) | |
| mannitol | 250 mg |
| water for injection | 5 ml. |

Example 5

Treatment of Patients

"A Multinational, Randomized, Double-Blind, Placebo-Controlled, Parallel-Group, Dose-Ranging, Safety and Efficacy Trial With Intravenous Bolus Injections of Zoledronate In the Treatment of Postmenopausal Osteoporosis"

This was a dose and dose regimen-finding 12 month trial of iv zoledronic acid in patients with postmenopausal osteoporosis. Three hundred and fifty one patients were randomized to six study arms. Patients who had recent exposure to bone active drugs, e.g. bisphosphonates, estrogen, calcitonin, raloxifene, or a history of metabolic bone diseases were excluded. All patients were evaluated at baseline and in 3-monthly visits. Zoledronic acid or placebo was administered as a bolus iv injection into a peripheral vein over 5 minutes at every visit.

Efficacy was ascertained by measurement of percent change from baseline in bone mineral density (BMD) measured by dual energy X-ray absorptiometry (DEXA) as compared to placebo, at 6, 9, and 12 months.

As a special safety measure trans-iliac bone biopsies were obtained in a subset of patients from all study arms at 12 months, and X-rays of the thoracic and lumbar spine from all study participants were evaluated at baseline and at 12 months for the occurrence of incident vertebral fractures.

Additionally, the degree and duration of suppression of biochemical markers of bone turnover—parathyroid hormone (PTH), bone specific alkaline phosphatase (BSAP), serum C-telopeptide (CTX), serum osteocalcin, urine N-telopeptide (NTX)/creatinine ratio, urine deoxypyridinoline (d-pyd)/creatinine ratio, urine pyridinoline (pyd)/creatinine ratio—was obtained every 3 months and measured in a central laboratory.

Study Arms
- Placebo
- 0.25 mg zoledronic acid every 3 months
- 0.5 mg zoledronic acid every 3 months
- 1.0 mg zoledronic acid every 3 months
- 2.0 mg zoledronic acid every 6 months
- 4.0 mg zoledronic acid every 12 months The 12 month results showed that all treatment arms demonstrated a percent change from baseline in BMD significantly ($p<0.001$) greater than placebo and not dissimilar one from another.

Summary of stepwise multiple comparisons of the active doses of zoledronate versus placebo for percent change from baseline in bone mineral density of the lumbar spine; postero anterior (L1-L4) at 12 months Confirmatory analysis ITT population

| Step Number | Most significant contrast | Difference | Standard error of difference | Lower 97.5% confidence limit | p-value |
|---|---|---|---|---|---|
| 1 | zoledronate 4 × 0.25 mg - placebo | 5.1 | 0.55 | 3.7 | <0.001 |
| 2 | zoledronate 4 × 0.5 mg - placebo | 4.9 | 0.56 | 3.5 | <0.001 |
| 3 | zoledronate 1 × 4.0 mg - placebo | 4.6 | 0.53 | 3.3 | <0.001 |
| 4 | zoledronate 4 × 1.0 mg - placebo | 4.5 | 0.55 | 3.2 | <0.001 |
| 5 | zoledronate 2 × 2.0 mg - placebo | 4.2 | 0.57 | 3.1 | <0.001 |

Note: Stepwise multiple comparison of the active doses of zoledronate versus placebo at a one-sided multiple alpha level of 2.5% adjusting for multiple comparisons according to Marcus, Peritz and Gabriel (1976)

Bone mineral density increased compared to placebo at the spine, hip, distal radius, and "total body". Suppression of biochemical markers of bone formation and bone resorption confirmed and supported the BMD results, demonstrating suppression of bone turnover to the pre-menopausal level throughout the 6 and 12 month dosing intervals.

The BMD data indicate that zoledronic acid dose administration as infrequent as every 6 or 12 months can safely result in a statistically significant and medically relevant bone mass increase. It is believed that these data further indicate that a continued preservation of new bone beyond one year, without additional dose administration, is likely or that further bone mass increase is possible. It is also believed that re-treatment in additional cycles of every 6 month, 12 month, or less frequent dose administration will lead to further BMD increase. A reduction of risk of osteoporotic fracture is expected to accompany the bone mass increases.

The invention claimed is:

1. A method for the treatment of conditions of abnormally increased bone turnover in a patient in need of such treatment which comprises intermittently administering an effective amount of 1-hydroxy-2-(imidazol-1-yl)ethane-1,1-diphosphonic acid or pharmaceutically acceptable salt thereof, or any hydrate thereof to the patient via intravenous administration, wherein the administrations of 1-hydroxy-2-(imidazol-1-yl)ethane-1,1-diphosphonic acid or pharmaceutically acceptable salt thereof, or any hydrate thereof is about once a year.

2. The method of claim 1 for the treatment of osteoporosis wherein the administrations of the 1-hydroxy-2-(imidazol-1-yl)ethane-1,1-diphosphonic acid or pharmaceutically acceptable salt thereof, or any hydrate thereof is about once a year.

3. The method of claim 1 wherein the 1-hydroxy-2-(imidazol-1-yl)ethane-1,1-diphosphonic acid or pharmaceutically acceptable salt thereof, or any hydrate thereof is in a unit dosage form adapted for parenteral administration which comprises from about 1 mg to about 10 mg of 1-hydroxy-2-(imidazol-1-yl)ethane-1,1-diphosphonic acid or pharmaceutically acceptable salt thereof, or any hydrate thereof.

4. The method of claim 3, wherein the unit dosage form comprises from about 1 mg to about 5 mg.

5. The method of claim 3, wherein the unit dosage form comprises from about 5 mg to about 10 mg.

6. The method of claim 4, wherein the unit dosage form comprises about 5 mg.

7. A method for the treatment of conditions of abnormally increased bone turnover in a patient in need of such treatment which comprises intermittently administering an effective amount of 1-hydroxy-2-(imidazol-1-yl)ethane-1,1-diphosphonic acid or pharmaceutically acceptable salt thereof, or any hydrate thereof to the patient via intravenous administration, wherein the administrations of 1-hydroxy-2-(imidazol-1-yl)ethane-1,1-diphosphonic acid or pharmaceutically acceptable salt thereof, or any hydrate thereof is about once every two years.

8. The method of claim 7 wherein the 1-hydroxy-2-(imidazol-1-yl)ethane-1,1-diphosphonic acid or pharmaceutically acceptable salt thereof, or any hydrate thereof is in a unit dosage form adapted for parenteral administration which comprises from about 1 mg to about 10 mg of 1-hydroxy-2-(imidazol-1-yl)ethane-1,1-diphosphonic acid or pharmaceutically acceptable salt thereof, or any hydrate thereof.

9. A method for the treatment of conditions of abnormally increased bone turnover in a patient in need of such treatment which comprises intermittently administering an effective amount of 1-hydroxy-2-(imidazol-1-yl)ethane-1,1-diphosphonic acid or pharmaceutically acceptable salt thereof, or any hydrate thereof to the patient via intravenous administration, wherein the administrations of 1-hydroxy-2-(imidazol-1-yl)ethane-1,1-diphosphonic acid or pharmaceutically acceptable salt thereof, or any hydrate thereof is less frequent than about once a year.

* * * * *